(12) United States Patent
Fieni (10) Patent No.: US 11,260,054 B2
(45) Date of Patent: Mar. 1, 2022

(54) METHODS OF TREATMENT OF CANCER

(71) Applicant: Pano Therapeutics, Inc., San Francisco, CA (US)

(72) Inventor: Francesca Fieni, San Francisco, CA (US)

(73) Assignee: Pano Therapeutics, Inc., San Francisco, CA (US)

( * ) Notice: Subject to any disclaimer, the term of this patent is extended or adjusted under 35 U.S.C. 154(b) by 0 days.

(21) Appl. No.: 17/105,306

(22) Filed: Nov. 25, 2020

(65) Prior Publication Data

US 2021/0154191 A1 May 27, 2021

Related U.S. Application Data

(63) Continuation of application No. PCT/US2019/034566, filed on May 30, 2019.

(60) Provisional application No. 62/679,643, filed on Jun. 1, 2018.

(51) Int. Cl.
| | |
|---|---|
| *A61K 31/4965* | (2006.01) |
| *A61P 35/00* | (2006.01) |
| *A61K 9/00* | (2006.01) |
| *A61K 45/06* | (2006.01) |

(52) U.S. Cl.
CPC ........ *A61K 31/4965* (2013.01); *A61K 9/0019* (2013.01); *A61K 9/0053* (2013.01); *A61K 45/06* (2013.01); *A61P 35/00* (2018.01)

(58) Field of Classification Search
USPC .................................................. 514/255.06
See application file for complete search history.

(56) References Cited

U.S. PATENT DOCUMENTS

| | | |
|---|---|---|
| 2006/0160746 A1 | 7/2006 | Gorin |
| 2012/0108494 A1 | 5/2012 | Gorin |

OTHER PUBLICATIONS

Murai (Production of New amilorides as potent inhibitors of mitochondrial respiratory complex I, Bioscience, Biotechnology, and Biochemistry, 2015).*
Urra (The Mitochrondrial Complex (I)ty of Cancer, Frontiers in Oncology, Jun. 2017, vol. 7, Article 118, pp. 1-8).*
Viale (Tumors and Mitochondrial Respiration: A neglected Connection, Cancer Research, vol. 75, Issue 18, 2015).*
Katagiri (HIF-1 maintains a functional relationship between pancreatic cancer cells and stromal fibroblasts by upregulating expression and secretion of Sonic hedgehog, Oncotarget, Jan. 2018, vol. 9, (No. 12), pp. 10525-10535).*
Long (Overcoming Drug Resistance in Pancreatic Cancer, Expert Opin Ther Targets. Jul. 2011 ; 15(7): 817-828 renumbered pp. 1-17).*
American Cancer Society "Cancer Facts & Figures 2016,", 72 pages.
Brand, M.D. et al. (Oct. 11, 2016, e-pub. Sep. 22, 2016). "Suppressors of Superoxide-H2O2 Production at Site IQ of Mitochondrial Complex I Protect Against Stem Cell Hyperplasia and Ischemia-Reperfusion Injury," Cell Metabolism 24(4):582-592, 26 pages.
Duffy, M.J. (Apr. 2001). "Carcinoembryonic Antigen as a Marker For Colorectal Cancer: Is It Clinically Useful?" Clinical Chem. 47(4):624-630.
Höeckel, M. et al. (Oct. 1, 1996). "Association Between Tumor Hypoxia and Malignant Progression In Advanced Cancer Of The Uterine Cervix," Cancer Res 56(19):4509-4515.
International Preliminary Report on Patentability, dated Dec. 1, 2020, for PCT Application No. PCT/US2019/034566, filed May 30, 2019, 5 pages.
International Search Report and Written Opinion, dated Aug. 12, 2019, for PCT Application No. PCT/US2019/034566, filed May 30, 2019, 7 pages.
Ito, T. et al. (Jun. 16, 2015, e-pub. Jun. 5, 2015). "Identification of the Binding Position of Amilorides in the Quinone Binding Pocket of Mitochondrial Complex I," Biochem. 54(23):3677-3686.
McKeown, S.R. (Mar. 2014). "Defining Normoxia, Physoxia and Hypoxia In Tumours-Implications For Treatment Response," Br J Radiol. 87(1035):20130676, 12 pages.
Muz, B. et al. (Dec. 11, 2015). "The role Of Hypoxia In Cancer Progression, Angiogenesis, Metastasis, and Resistance To Therapy," Hypoxia 3:83-92.
Wang, Y.-W. et al. (Aug. 22, 2017). "Metformin: A Review Of Its Potential Indications," Drug Design, Development and Therapy 11:2421-2429.
U.S. Appl. No. 15/733,874, Kirichok et al, filed Nov. 30, 2020. (Copy not submitted herewith pursuant to the waiver of 37 C.F.R. § 1.98(a)(2)(iii) issued by the Office on Sep. 21, 2004.).
Ashton, T.M. et al. (Jun. 1, 2018, e-pub. Feb. 2, 2018). "Oxidative Phosphorylation as an Emerging Target in Cancer Therapy," Clinical Cancer Research 24(11):2482-2490.
Frouws, M.A. et al. (2017). "No Association Between Metformin Use and Survival in Patients With Pancreatic Cancer," Medicine 96:10, 6 pages.
Lipner, M.B. et al. (Jan. 13, 2016). "Metformin Treatment Does Not Inhibit Growth of Pancreatic Cancer Patient-Derived Xenografts," PLOS One 11(1):e014713, 15 pages.
Reni, M. et al. (Mar. 1, 2016, e-pub. Oct. 12, 2015). "(Ir)relevance of Metformin Treatment in Patients With Metastatic Pancreatic Cancer: An Open-Label, Randomized Phase II Trial," Clinical Cancer Research 22(5):1076-1085.
Sivalingam, V.N. et al. (2020). "Hypoxia and Hyperglycaemia Determine Why Some Endometrial Tumours Fail To Respond to Metformin," British Journal of Cancer 122:62-71.

(Continued)

*Primary Examiner* — Kathrien A Cruz
(74) *Attorney, Agent, or Firm* — Morrison & Foerster LLP (57) ABSTRACT

Provided herein are methods of treating cancer, including colorectal cancer, pancreatic cancer, and cancer associated with a hypoxic tumor. Also provided are methods of treating cancer, including colorectal cancer, pancreatic cancer, and cancer associated with a hypoxic tumor with a combination of treatments.

30 Claims, 4 Drawing Sheets

(56) References Cited

OTHER PUBLICATIONS

Viale, A. et al. (Oct. 30, 2014). "Oncogene Ablation-Resistant Pancreatic Cancer Cells Depend On Mitochondrial Function," Nature 514(7524):628-632, 31 pages.
Wheaton, W.W. et al. (May 13, 2014). "Metformin Inhibits Mitochondrial Complex I of Cancer Cells To Reduce Tumorigenesis," eLife 3:e02242, 18 pages.

* cited by examiner

FIG. 1

FIG. 2A Cpds IC50 in PANC-1 Cell Line (72h)

FIG. 2B Cpds IC50 in MiaPaCa-2 Cell Line (72h)

METHODS OF TREATMENT OF CANCER

CROSS-REFERENCE TO RELATED APPLICATIONS

This application is a continuation application of International Application No. PCT/US2019/034566, filed May 30, 2019; which claims the priority benefit of U.S. Provisional Application No. 62/679,643, filed Jun. 1, 2018; the contents of each of which is incorporated herein by reference in its entirety.

FIELD

The present disclosure relates to methods of treating cancer, including colorectal cancer, pancreatic cancer, and cancer associated with a hypoxic tumor. The disclosure further relates to methods of treating cancer, including colorectal cancer, pancreatic cancer, and cancer associated with a hypoxic tumor with a combination of treatments.

BACKGROUND

Colorectal cancer is one of the top four most common types of cancers in both males and females, and can be especially deadly when it metastasizes to distant parts of the body. The 5 year survival rate under this circumstance is only 14% (American Cancer Society. Colorectal Cancer Facts & FIGS. 2017-2019. Atlanta: American Cancer Society; 2017).

Although pancreatic cancer is less common than colorectal cancer, it is notoriously difficult to treat. According to the American Cancer Society, for all stages of pancreatic cancer combined, the 1- and 5-year relative survival rates are 29% and 7%, respectively. Even for the small percentage of people diagnosed with local disease (9%), the 5-year survival is only 27%. More than half (53%) of patients are diagnosed at a distant stage, for which 1- and 5-year survival is 15% and 2%, respectively (American Cancer Society. Cancer Facts & FIGS. 2016. Atlanta: American Cancer Society; 2016).

Hypoxia, or a decreased level of oxygen, is an independent, adverse prognostic factor for tumor progression (Hoeckel et al. Cancer Res 1996, 56:4509-15). For most cells, including most cancer cells, hypoxia leads to anti-proliferative effects such as apoptosis and necrosis, but for a minority of cancer cells, hypoxia leads to an adaptive response with aggressive phenotypes, increase tumor progression, and increase treatment resistance. In fact, the role of hypoxia in the phenomenon of therapy resistance has been acknowledged for at least 60 years (Muz, Hypoxia, 2015, 3:83-92).

Given the common, but deadly nature of colorectal cancer; the terrible survival rates of pancreatic cancer; and the significantly worse prognosis for cancerous tumors with higher levels of hypoxia, there is a need for improved treatments for these cancers.

BRIEF SUMMARY

Provided herein is a method of treating cancer in a subject, comprising administering to the subject an effective amount of a compound of Formula (I):

or a tautomer thereof, or a salt of any of the foregoing, wherein: X is halo; Y is wherein: * indicates the point of attachment to the carbonyl of the parent structure and ** indicates the point of attachment to $(CH_2)_{4-7}$—Y; and Z is $C_1$-$C_6$alkyl or phenyl, and wherein the cancer is associated with a hypoxic tumor. In some embodiments, the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma. In some embodiments, the cancer is pancreatic cancer or colorectal cancer. In some embodiments, the hypoxic tumor is a solid tumor.

In some embodiments, a plurality of cells in the hypoxic tumor express one or more hypoxia-inducible factor (HIF) proteins; one or more messenger ribonucleic acids (mRNAs) encoding a HIF protein; or one or more hypoxia-inducible factor (HIF) proteins and one or more messenger ribonucleic acids (mRNAs) encoding a HIF protein. In some embodiments, the one or more HIF proteins; the one or more mRNAs encoding a HIF protein; or the one or more HIF proteins and the one or more mRNAs encoding a HIF protein are expressed at a higher level than in a normal tissue. In some embodiments, the normal tissue is (a) non-cancerous muscle tissue; (b) derived from the same tissue or organ; or (c) healthy tissue located near the hypoxic tumor.

In some embodiments, the hypoxic tumor has one or more of the following hypoxic conditions: (a) a median oxygen level below 2%; (b) a median partial pressure of oxygen ($pO_2$) of about or less than about 15 mmHg; (c) a median $pO_2$ that is less than 30% of the $pO_2$ of a normal tissue; and (d) the percentage of $pO_2$ measurements of the hypoxic tumor that equal less than 10 mm Hg ($HP_{10}$) is greater than 50%. In some embodiments, the normal tissue is (a) non-cancerous muscle tissue; (b) derived from the same tissue or organ; or (c) healthy tissue located near the hypoxic tumor.

In some embodiments, the method further comprises measuring the $pO_2$ or percent $O_2$ of the hypoxic tumor.

Also provided herein is a method of treating pancreatic or colorectal cancer in a subject, comprising administering to the subject an effective amount of a compound of Formula (I):

(I)

or a tautomer thereof, or a salt of any of the foregoing, wherein: X is halo; Y is wherein: * indicates the point of attachment to the carbonyl of the parent structure and ** indicates the point of attachment to $(CH_2)_{4-7}$—Y; and Z is $C_1$-$C_6$alkyl or phenyl. In some embodiments, the cancer is pancreatic cancer. In some embodiments, the cancer is colorectal cancer.

In some embodiments of any of the methods described herein, the compound is or a tautomer thereof, or a salt of any of the foregoing. In some embodiments of any of the methods described herein, the compound is or a tautomer thereof, or a salt of any of the foregoing.

In some embodiments, the compound is administered orally or intravenously.

In some embodiments, the subject has had a prior treatment. In some embodiments, the cancer is resistant or refractory to the prior treatment. In some embodiments, the cancer is resistant to treatment with gemcitabine, docetaxel, paclitaxel, paclitaxel protein-bound particles, cisplatin, or radiation.

In some embodiments, the method further comprises administering radiation. In some embodiments, the method further comprises administering a second anticancer agent. In some embodiments, the second anticancer agent is a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor.

DETAILED DESCRIPTION

I. Definitions

As used herein, the singular form "a," "an," and "the" includes plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that embodiments, aspects and variations described herein also include "consisting" and/or "consisting essentially of" embodiments, aspects and variations.

The term "effective amount" used herein refers to an amount of a compound or composition sufficient to treat a specified disorder, condition or disease, such as ameliorate, palliate, lessen, and/or delay one or more of its symptoms. In reference to a cancer, an effective amount comprises an amount sufficient to cause the number of cancer cells present in a subject to decrease in number and/or size and/or to slow the growth rate of the cancer cells. In some embodiments, an effective amount is an amount sufficient to prevent or delay recurrence of the disease. In the case of cancer, the effective amount of the compound or composition may: (i) reduce the number of cancer cells; (ii) inhibit, retard, slow to some extent and preferably stop cancer cell proliferation; (iii) prevent or delay occurrence and/or recurrence of the cancer; and/or (iv) relieve to some extent one or more of the symptoms associated with the cancer.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "subject" refers to a mammal and includes, but is not limited to, human, bovine, horse, feline, canine, rodent, or primate. In one embodiment, the subject is a human.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. In reference to a cancer, the number of cancer cells present in a subject may decrease in number and/or size and/or the growth rate of the cancer cells may slow. In some embodiments, treatment may prevent or delay recurrence of the disease. In the case of cancer, the treatment may: (i) reduce the number of cancer cells; (ii) inhibit, retard, slow to some extent and preferably stop cancer cell proliferation; (iii) prevent or delay occurrence and/or recurrence of the cancer; and/or (iv) relieve to some extent one or more of the symptoms associated with the cancer. The methods of the invention contemplate any one or more of these aspects of treatment.

The term "simultaneous administration," as used herein, means that a first therapy and second therapy in a combination therapy are administered with a time separation of no more than about 15 minutes, such as no more than about any of 10, 5, or 1 minutes.

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first.

As used herein, the term "concurrent administration" means that the administration of the first therapy and that of a second therapy in a combination therapy overlap with each other.

As used herein, the term "hypoxic" or "hypoxia" refers to a condition wherein the oxygen concentration is lower than a normal, physiological level. As used herein, the term "normoxic" or "normoxia" refers to a condition used in cell culture wherein the oxygen concentration is approximately the same as atmospheric oxygen. A normoxic condition has a higher oxygen concentration than a normal, physiological level. As used herein, the term "hypoxic tumor" means a tumor comprising a plurality of cells that have been deprived of oxygen or where the oxygen concentration is significantly lower than in a normal, healthy tissue.

Unless defined otherwise, all terms of art, notations and other technical and scientific terms or terminology used herein are intended to have the same meaning as is commonly understood by one of ordinary skill in the art to which the claimed subject matter pertains.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

II. Methods of Treatment

Provided herein are methods of treating cancer, such as methods of treating pancreatic cancer, colorectal cancer, or cancer associated with a hypoxic tumor. In some embodiments, the method comprises administering a compound disclosed herein, such as a compound of Formula (I), or any embodiment, variation, or aspect thereof, including a tautomer thereof, or a salt, such as a pharmaceutical salt, of any of the foregoing. In some embodiments, the method comprises administering a pharmaceutical composition disclosed herein, such as a pharmaceutical composition comprising a compound discloses herein.

In some embodiments, provided herein is a method of treating colorectal cancer, comprising administering a compound disclosed herein. In some embodiments, the colorectal cancer is colon cancer. In some embodiments, the colorectal cancer is rectal cancer. In some embodiments, the colorectal cancer is a carcinoma.

The present compounds or salts thereof are believed to be effective for treating a cancer, such as colorectal cancer, that result in high expression of carcinoembryonic antigen (CEA) even though patients with high preoperative concentrations of CEA have a worse outcome than those with low concentrations of the marker (Duffy, Clinical Chem, 2001, 47(4): 624-630). In some embodiments, the subject has a blood CEA level of about or at least about 5 μg/L, such as about or at least about 6 μg/L, 7 μg/L, 8 μg/L, 9 μg/L, 10 μg/L, 20 μg/L, 30 μg/L, 40 μg/L, 50 μg/L 100 μg/L, 200 μg/L, or 300 μg/L. In some embodiments, the subject has a blood carcinoembryonic antigen (CEA) level of about or at least about 10 μg/L.

In some embodiments, provided herein is a method of treating pancreatic cancer, comprising administering a compound disclosed herein. In some embodiments, the pancreatic cancer is an exocrine pancreatic cancer. In some embodiments, the pancreatic cancer is a carcinoma. In some embodiments, the pancreatic cancer expresses a p53 gene comprising a mutation. In some embodiments, the p53 gene mutation is at nucleic acid 742 or 818. In some embodiments, the gene mutation is 742C>T or 818G>A. In some embodiments, the pancreatic cancer expresses a mutated p53 protein. In some embodiments, the p53 protein mutation is at amino acid 248 or 273. In some embodiments, the p53 protein mutation is R248W or R273H.

In some embodiments, provided herein is a method of treating cancer, comprising administering a compound disclosed herein, wherein the cancer is associated with a hypoxic tumor. In some embodiments, the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma. In some embodiments, the cancer is pancreatic cancer or colorectal cancer. In some embodiments, the cancer is colon cancer. In some embodiments, the cancer is prostate cancer. In some embodiments, the cancer is a carcinoma. In some embodiments, the hypoxic tumor is a solid tumor.

In some embodiments, a plurality of cells in the hypoxic tumor express one or more hypoxia-inducible factor (HIF) proteins and/or one or more messenger ribonucleic acids (mRNAs) encoding a HIF protein. In some embodiments, the one or more HIF proteins and/or one or more mRNAs encoding a HIF protein are expressed at a higher level than a normal tissue. In some embodiments, the HIF protein is HIF-1 or HIF-2. In some embodiments, the HIF protein is HIF-1a.

In some embodiments the hypoxic tumor has one or more hypoxic conditions. In some embodiments, the hypoxic condition occurs for more than about 2 minutes, such as more than about 5 minutes, 10 minutes, 20 minutes, 40 minutes, 1 hour, 2 hours, 4 hours, 8 hours, 12 hours, 24 hours, 36 hours, 48 hours, or 72 hours. In some embodiments, the hypoxic condition occurs for 2 minutes to 72 hours. In some embodiments, the hypoxic condition occurs for 2 minutes to 1 hour. In some embodiments, the hypoxic condition fluctuates. In some embodiments, more than about 10% of the cells of the hypoxic tumor are hypoxic, such as more than about 20%, 25%, 30%, 40%, 50%, 60%, 75%, or 85%.

The level of hypoxia within a tumor varies by cancer type and stage and from patient to patient. Reported exemplary values of median partial pressure of oxygen ($pO_2$) and median % oxygen in human tumors and related normal tissues, and well as the fold $pO_2$ decrease in tumor from related normal tissues is shown in Table 1 (adapted from McKeown, Br J Radiol, 2014, 87:20130674 The fold reduction of tumor versus normal tissue shown in Table 1 is based on data presented in Table 1 except for prostate cancer wherein the normal tissue is contemporaneous measurements in the psoas muscle or measurements from normal prostate in bladder cancer patients.

TABLE 1

Reported median tumor $pO_2$ and % oxygen in human tumors and related normal tissues

| Tumor type | Median tumor $pO_2$ (mmHg) | Median tumor % oxygen | Median normal tissue $pO_2$ (mmHg) | Median normal tissue % oxygen | Fold $pO_2$ decrease |
| --- | --- | --- | --- | --- | --- |
| Brain | 12.0 | 1.7 | 26.0 | 3.4 | 2.0 |
| Head and neck cancer | 10.0 | 1.3 | | 5.9 | 4.5 |
| | 12.2 | 1.6 | 40.0 | 5.3 | 3.3 |
| | 14.7 | 1.9 | 43.8 | 5.8 | 3.0 |
| | 14.6 | 1.9 | 51.2 | 6.7 | 3.5 |
| Lung cancer | 14.3 | 1.9 | | 5.6 | 3.0 |
| | 16.6 | 2.2 | 42.8 | 5.6 | 2.6 |
| Breast cancer | 10.0 | 1.3 | 52.0 | 6.8 | 5.2 |
| Cervical cancer | 9.0 | 1.2 | 42.0 | 5.5 | 4.7 |
| Liver | 6.0 | 0.8 | 30.0 | 3.9 | 5.0 |
| Pancreatic cancer | 2.7 | 0.4 | 51.6 | 6.8 | 19.1 |
| | 2.0 | 0.3 | | | 22.7 |
| Prostate cancer | 2.4 | 0.3 | 30.0 | 3.9 | 12.5 |
| | 4.5 | 0.6 | | | 6.7 |
| | 9.4 | 1.2 | 26.2 | 3.4 | 2.8 |
| Vulval cancer | 11.0 | 1.4 | | | |
| | 13.0 | 1.7 | | | |
| | 11.0 | 1.4 | | | |
| | 10.0 | 1.3 | | | |
| Melanoma | 11.6 | 1.5 | 40.5 | 5.3 | 3.5 |
| Renal cell carcinoma | 10.0 | 1.3 | 37.6 | 4.9 | 3.8 |
| Rectal carcinoma | 32.0 | 4.2 | 52.0 | 6.8 | 1.6 |
| | 19.0 | 2.5 | 52.0 | 6.8 | 2.7 |
| Sarcoma | 14.0 | 1.8 | 51.0 | 6.7 | 3.6 |
| Averages or total | 10.3 | 1.4 | 45.8 | 6.0 | 4.6 |
| Range of medians | 2.0-32.0 | 0.3-4.2 | 26.0-51.6 | 3.4-6.8 | |

In some embodiments, the hypoxic condition is a median oxygen level below 2%, such as below 1.5%, 1%, 0.8%, 0.6%, or 0.5%. In some embodiments, the hypoxic tumor has a median oxygen level below 1%. In some embodiments, the hypoxic tumor has a median oxygen level below 0.5%.

In some embodiments, the hypoxic condition is a median $pO_2$ of about or less than about 15 mmHg, such as about or less than about 10 mmHg, 8 mmHg, 5 mmHg, or 3 mmHg. In some embodiments, the hypoxic tumor has a median $pO_2$ of less than about 8 mmHg. In some embodiments, the hypoxic tumor has a median $pO_2$ of less than about 3 mmHg.

In some embodiments, the hypoxic condition is the percentage of $pO_2$ measurements of the hypoxic tumor that equal less than 10 mm Hg ($HP_{10}$) is greater than 50%, such as greater than 55%, 60%, 65%, 70%, 75%, or 80%. In some embodiments, the $HP_{10}$ is greater than 80%. In some embodiments, the hypoxic condition is the percentage of $pO_2$ measurements of the hypoxic tumor that equal less than 5 mm Hg ($HP_5$) is greater than 50%, such as greater than 55%, 60%, 65%, 70%, 75%, or 80%. In some embodiments, the $HP_5$ is greater than 80%. In some embodiments, the hypoxic condition is the percentage of $pO_2$ measurements of the hypoxic tumor that equal less than 2.5 mm Hg ($HP_{2.5}$) is greater than 50%, such as greater than 55%, 60%, 65%, 70%, 75%, or 80%. In some embodiments, the $HP_{2.5}$ is greater than 80%.

In some embodiments, the hypoxic condition is a median $pO_2$ that is less than about 30% of the $pO_2$ of a normal tissue, such as less than about 25%, 20%, 10%, 5%, 2.5%, 1%, 0.5%, or 0.1%. In some embodiments, the normal tissue is normal tissue in the subject. In some embodiments, the normal tissue is normal tissue in a healthy subject. In some embodiment, the normal tissue is an average of normal tissue from a plurality of subjects.

In some embodiments, the normal tissue and the cancer are derived from the same tissue or organ. In some embodiments, the cancer is leukemia and the normal tissue is healthy bone marrow; brain cancer and the normal tissue is healthy brain tissue; breast cancer and the normal tissue is healthy breast tissue; cervical cancer and the normal tissue is healthy cervical tissue; renal cancer and the normal tissue is healthy kidney tissue; liver cancer and the normal tissue is healthy liver tissue; lung cancer and the normal tissue is healthy lung tissue; pancreatic cancer and the normal tissue is healthy pancreatic tissue; colorectal cancer and the normal tissue is healthy colon or rectal tissue; head and neck cancer and the normal tissue is healthy head or neck tissue; prostate cancer and the normal tissue is healthy prostate tissue; vulvar cancer and the normal tissue is healthy vulvar tissue; or skin cancer and the normal tissue is healthy skin tissue. In some embodiments, the cancer is pancreatic cancer and the normal tissue is healthy pancreatic tissue.

In some embodiments, the normal tissue is non-cancerous muscle tissue. The level of tumor to muscle $pO_2$ has been shown to be a strong predictor of prognosis (reviewed in McKeown, Br J Radiol, 2014, 87:20130676). In some embodiments, the hypoxic tumor is located in a different tissue than the cancer was derived from. In such embodiments, it may be appropriate to compare the hypoxic tumor to nearby healthy tissue. Accordingly, in some embodiments, the hypoxic tumor is located in the bone marrow of the subject and the normal tissue is healthy bone marrow; the brain of the subject and the normal tissue is healthy brain tissue; the breast of the subject and the normal tissue is healthy breast tissue; the cervix of the subject and the normal tissue is healthy cervical tissue; the kidney of the subject and the normal tissue is healthy kidney tissue; the liver of the subject and the normal tissue is healthy liver tissue; the lung of the subject and the normal tissue is healthy lung tissue; the pancreas of the subject and the normal tissue is healthy pancreatic tissue; the colon of the subject and the normal tissue is healthy colon tissue; the rectum of the subject and the normal tissue is rectal tissue; the head of the subject and the normal tissue is healthy head tissue; the neck of the subject and the normal tissue is healthy neck tissue; the prostate of the subject and the normal tissue is healthy prostate tissue; the vulva of the subject and the normal tissue is healthy vulvar tissue; or the skin of the subject and the normal tissue is healthy skin tissue. In some embodiments, the hypoxic tumor is located in the pancreas and the normal tissue is healthy pancreatic tissue.

In some embodiments, the methods described herein further comprise obtaining information regarding the hypoxic status of the hypoxic tumor. In some embodiments, the information is one or more of the following: detection of hypoxia biomarkers, such as HIF gene or protein expression or measurement of the $pO_2$ or percent $O_2$ of the hypoxic tumor. In some embodiments, the methods described herein further comprise measuring the $pO_2$ or percent $O_2$ of the hypoxic tumor. Methods of measuring the $pO_2$ are known in the art. For example, in some embodiments, measuring or measurement of the $pO_2$ or percent $O_2$ comprises using positron emission tomography (PET) imaging, computerized tomography (CT) imaging, polarographic $O_2$ sensors, blood oxygen level dependent (BOLD) magnetic resonance imaging (MRI), dynamic contrast-enhanced (DCE) MRI, or electron paramagnetic resonance (EPR) oximetry. In some embodiments, the subject was administered an agent that allows detection of hypoxia. In some embodiments, the subject was administered an agent that allows detection of hypoxia and hypoxia was detected in a sample of the hypoxic tumor. In some embodiments, the measuring (or measurement) is performed in vitro. In some embodiments, the in vitro measuring (or measurement) comprises detecting an exogenous hypoxic marker in a sample of the hypoxic tumor. In some embodiments, the in vitro measuring (or measurement) comprises detecting an endogenous hypoxic marker in a sample of the hypoxic tumor. In some embodiments, the measuring (or measurement) is performed in vivo. In some embodiments, the subject is not under general anesthesia during the measuring. In some embodiments, the subject is under local anesthesia during the measuring.

In some embodiments, a compound or salt thereof described herein or a composition described herein may be used in a method of treating cancer in a subject, wherein the subject has had a prior treatment. In the embodiments, the cancer is a recurrent cancer. In some embodiments, the cancer is resistant or refractory to the prior treatment. In some embodiments, the cancer has progressed on the prior treatment. In some embodiments, the prior treatment was treatment with radiation, surgery, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, a tyrosine kinase inhibitor, or combinations thereof. In some embodiments, the cancer is resistant to treatment with radiation, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, a tyrosine kinase inhibitor, or combinations thereof. In some embodiments, the cancer is resistant to treatment with gemcitabine, docetaxel, paclitaxel, paclitaxel protein-bound particles, cisplatin, or radiation. In some embodiments, the cancer is resistant to treatment with cisplatin.

In some embodiments, administration of a compound disclosed herein reduces tumor growth, tumor proliferation, or the formation of metastatic tumors in the subject. In some embodiments, tumor growth is slowed or arrested. In some embodiments, tumor growth is reduced at least about 10%, such as at least about 20%, 30%, 40%, 50%, 60%, 70%, 80%, or 90%. In some embodiments, the tumor is reduced in size. In some embodiments, tumor size is reduced at least about 10%, such as at least about 20%, 30%, 40%, 50%, 60%, 70%, 80%, or 90%. In some embodiments, formation of a metastatic tumor is prevented or slowed. Tumor growth, tumor proliferation, or the formation of metastatic tumors may be compared to the tumor growth, tumor proliferation, or formation of metastatic tumors in the subject prior to administration of the compound or to tumor growth, tumor proliferation, or the formation of metastatic tumors in a similar subject or group of subjects. Methods of measuring tumor growth, tumor proliferation, or the formation of metastatic tumors are known in the art, for example by repeated imaging of the subject.

The dose, dosing schedule, or dosing duration of the compound administered to a subject may vary with the particular compound, the method of administration, and the particular disease being treated. In some embodiments, the amount of the compound is a therapeutically effective amount. The effective amount of the compound may in one aspect be a dose of between about 0.01 and about 100 mg/kg. Effective amounts or doses of the compound may be ascertained by known methods, such as modeling, dose escalation, or clinical trials, taking into account factors, e.g., the mode or route of administration or drug delivery, the pharmacokinetics of the agent, the severity and course of the disease to be treated, the subject's health status, condition, and weight.

The compound or pharmaceutical composition comprising the compound can be administered to the subject via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, the compound is administered orally. In some embodiments, the compound is administered intravenously.

In some embodiments, the subject is a mammal. In some embodiments, the subject is a human, primate, dog, cat, rabbit, or rodent. In some embodiments, the subject is a human. In some embodiments, the subject has a cancer disclosed herein.

Also provided herein are uses of a compound described herein, or pharmaceutical compositions comprising a compound described herein, in the manufacture of a medicament for the treatment of a disease described herein. Further provided herein are uses of a compound described herein, or a pharmaceutical composition comprising a compound described herein, in a method of treatment of a disease described herein, as well as pharmaceutical compositions for use in a method of treatment described herein.

In some embodiments, the method further comprises administering a second cancer treatment. In some embodiments, the second cancer treatment is radiation, surgery, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor. In some embodiments, the method further comprises administering radiation. In some embodiments, the method further comprises administering radiation and surgery. Either the compound described herein, or a pharmaceutically acceptable salt thereof, or a pharmaceutical composition described herein; or the second cancer treatment may be administered first.

In some embodiments, a compound described herein, or a pharmaceutically acceptable salt thereof, or a pharmaceutical composition described herein and a second cancer treatment are sequentially administered, concurrently administered or simultaneously administered. In certain embodiments, a compound described herein, or a pharmaceutically acceptable salt thereof, or a pharmaceutical composition described herein; and a second cancer treatment are administered with a time separation of about 15 minutes or less, such as about any of 10, 5, or 1 minutes or less. In certain embodiments, a compound described herein, or a pharmaceutically acceptable salt thereof, or a pharmaceutical composition described herein; and a second cancer treatment are administered with a time separation of about 15 minutes or more, such as about any of 20, 30, 45, 60, or more minutes. In certain embodiments, a compound described herein, or a pharmaceutically acceptable salt thereof, or a pharmaceutical composition described herein; and the second cancer treatment are administered simultaneously.

III. Compounds and Compositions and Formulations Thereof

In some embodiments, the compound is a compound of Formula (I):

or a tautomer thereof, or a salt of any of the foregoing, wherein:

X is halo;

Y is wherein:

\* indicates the point of attachment to the carbonyl of the parent structure and \*\* indicates the point of attachment to $(CH_2)_{4-7}$—Y; and

Z is $C_1$-$C_6$alkyl or phenyl.

In some embodiments, the compound is a compound of formula (I), wherein X is chloro or iodo.

In some embodiments, the compound is a compound of formula (I), wherein Y is In some such embodiments, Y is of the formula In some embodiments, Y is such as a Y containing four methylene groups, and X is chloro or iodo.

iodobenzyl)amino)pyrazine-2-carboxamide (5o), or (E)-3-amino-N-(amino((4-phenylbutyl)amino)methylene)-6-chloro-5-((4-iodobenzyl)amino)pyrazine-2-carboxamide (5 m); or a pharmaceutically acceptable salt thereof. In some embodiments, the compound is 3-amino-6-chloro-5-((4-chlorobenzyl)amino)-N-(4-(methyl(6-phenylhexyl)amino) butyl)pyrazine-2-carboxamide. In some embodiments, the compound is (E)-3-amino-N-(amino((4-phenylbutyl)amino) methylene)-6-chloro-5-((4-iodobenzyl)amino)pyrazine-2-carboxamide.

In certain embodiments, the compound is a compound listed in Table 1.

TABLE 1

| Structure | Name |
| --- | --- |
|  | (E)-3-amino-N-(amino((4-phenylbutyl)amino)methylene)-6-chloro-5-((4-iodobenzyl)amino)pyrazine-2-carboxamide "5m" |
|  | (E)-3-amino-N-(amino(octylamino)methylene)-6-chloro-5-((4-iodobenzyl)amino)pyrazine-2-carboxamide "5o" |
|  | 3-amino-6-chloro-5-((4-chlorobenzyl)amino)-N-(4-(methyl(6-phenylhexyl)amino)butyl)pyrazine-2-carboxamide "AA6" |

In some embodiments, the compound is a compound of formula (I), wherein Y is

In some embodiments, the compound is a compound of formula (I), wherein Y is and X is chloro or iodo.

In some embodiments, the compound is a compound of formula (I), wherein Z is $C_1$-$C_6$alkyl, such as methyl. In some embodiments, the compound is a compound of formula (I), wherein Z is phenyl. In some embodiments, Z is $C_1$-$C_6$alkyl, such as methyl, and X is chloro or iodo. In some embodiments, Z is phenyl and X is chloro or iodo.

In some embodiments, the compound is 3-amino-6-chloro-5-((4-chlorobenzyl)amino)-N-(4-(methyl(6-phenylhexyl)amino)butyl)pyrazine-2-carboxamide (AA6), (E)-3-amino-N-(amino(octylamino)methylene)-6-chloro-5-((4-

Also provided are salts of compounds referred to herein, such as pharmaceutically acceptable salts. Thus, salts, including pharmaceutically acceptable salts, of any of the compounds detailed herein, including those of Table 1 are embraced by this disclosure.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described, such as the compounds of Table 1. The structure or name is intended to embrace all possible stereoisomers of a compound depicted. Pharmaceutical compositions comprising a compound described herein are also intended, such as a pharmaceutical composition of a specific stereochemical form, or a pharmaceutical composition comprising two or more stereochemical forms, such as in a racemic mixture.

In some embodiments, the compound is a pharmaceutically acceptable salt of any of the compounds described herein. In some embodiments, a pharmaceutically acceptable salt is one or more salts of a given compound which possesses desired pharmacological activity of the free compound and which is neither biologically nor otherwise undesirable. In some embodiments, a pharmaceutically acceptable salt is one or more salts of a given compound which possesses desired pharmacological activity of the free compound and which is neither biologically nor otherwise undesirable. In some embodiments, a pharmaceutically acceptable salt includes a salt with an inorganic base, organic base, inorganic acid, organic acid, or basic or acidic amino acid.

In some embodiments, a pharmaceutical composition comprises a compound of Formula (I) or a compound of Table 1, or a pharmaceutically acceptable salt thereof. In some embodiments, the pharmaceutical composition comprises the compound and one or more pharmaceutically acceptable carriers. In some embodiments, the pharmaceutically acceptable carrier is a non-toxic, inert solid, semi-solid or liquid filler, diluent, encapsulating material, or formulation auxiliary of any type. Some examples of materials that can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition.

The compound or pharmaceutical composition comprising the compound may be formulated for administration via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal.

In some embodiments, the pharmaceutical composition is suitable for administration to a human. In some embodiments, the pharmaceutical composition is suitable for administration to a mammal such as, in the veterinary context, domestic pets, and agricultural animals.

The following formulations are merely exemplary and are in no way limiting.

Formulations suitable for oral administration can be (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

In some embodiments, the pharmaceutical composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

IV. Kits and Articles of Manufacture

The present disclosure further provides articles of manufacture comprising a compound described herein or a pharmaceutical composition described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprise a compound described herein or a pharmaceutical composition described herein. The kits may employ any of the compounds described herein. The kits may be used for any one or more of the methods or uses described herein, and, accordingly, may contain instructions for the treatment of any disease or described herein, for example for the treatment of cancer. In some embodiments, the instructions are for the treatment of pancreatic cancer, colorectal cancer, or cancer associated with a hypoxic tumor.

Kits generally comprise suitable packaging. The kits may comprise one or more containers comprising a compound described herein or a pharmaceutical composition described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound described herein or a pharmaceutical composition described herein to provide effective treatment of a subject

17 for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to a subject.

V. Exemplary Embodiments

Among the provided embodiments are:
1. A method of treating cancer in a subject, comprising administering to the subject an effective amount of a compound of Formula (I):

or a tautomer thereof, or a salt of any of the foregoing, wherein:
X is halo;
Y is wherein:
* indicates the point of attachment to the carbonyl of the parent structure and ** indicates the point of attachment to $(CH_2)_{4-7}$—Y; and
Z is $C_1$-$C_6$alkyl or phenyl, and wherein the cancer is associated with a hypoxic tumor.
2. The method of embodiment 1, wherein the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma.
3. The method of embodiment 1 or 2, wherein the cancer is pancreatic cancer or colorectal cancer.
4. The method of any one of embodiments 1-3, wherein the hypoxic tumor is a solid tumor.
5. The method of any one of embodiments 1-3, wherein a plurality of cells in the hypoxic tumor express one or more hypoxia-inducible factor (HIF) proteins; one or more messenger ribonucleic acids (mRNAs) encoding a HIF protein;

18 or one or more hypoxia-inducible factor (HIF) proteins and one or more messenger ribonucleic acids (mRNAs) encoding a HIF protein.
6. The method of embodiment 5, wherein the one or more HIF proteins; the one or more mRNAs encoding a HIF protein; or the one or more HIF proteins and the one or more mRNAs encoding a HIF protein are expressed at a higher level than in a normal tissue.
7. The method of any one of embodiments 1-6, wherein the hypoxic tumor has one or more of the following hypoxic conditions:
(a) a median oxygen level below 2%;
(b) a median partial pressure of oxygen ($pO_2$) of about or less than about 15 mmHg;
(c) a median $pO_2$ that is less than 30% of the $pO_2$ of a normal tissue; and
(d) the percentage of $pO_2$ measurements of the hypoxic tumor that equal less than 10 mm Hg ($HP_{10}$) is greater than 50%.
8. The method of embodiment 6 or 7, wherein the normal tissue is (a) non-cancerous muscle tissue; (b) derived from the same tissue or organ; or (c) healthy tissue located near the hypoxic tumor.
9. The method of any one of embodiments 1-8, further comprising measuring the $pO_2$ or percent $O_2$ of the hypoxic tumor.
10. A method of treating pancreatic or colorectal cancer in a subject, comprising administering to the subject an effective amount of a compound of Formula (I):

or a tautomer thereof, or a salt of any of the foregoing, wherein:
X is halo;
Y is wherein:
* indicates the point of attachment to the carbonyl of the parent structure and ** indicates the point of attachment to $(CH_2)_{4-7}$—Y; and
Z is $C_1$-$C_6$alkyl or phenyl.
11. The method of embodiment 10, wherein the cancer is pancreatic cancer.
12. The method of embodiment 10, wherein the cancer is colorectal cancer.

13. The method of any one of embodiments 1-12, wherein the compound is or a tautomer thereof, or a salt of any of the foregoing.

14. The method of any one of embodiments 1-12, wherein the compound is or a tautomer thereof, or a salt of any of the foregoing.

15. The method of any one of embodiments 1-14, wherein the compound is administered orally or intravenously.

16. The method of any one of embodiments 1-15, wherein the subject has had a prior treatment.

17. The method of embodiment 16, wherein the cancer is resistant or refractory to the prior treatment.

18. The method of any one of embodiments 1-17, the cancer is resistant to treatment with gemcitabine, docetaxel, paclitaxel, paclitaxel protein-bound particles, cisplatin, or radiation.

19. The method of any one of embodiments 1-18, further comprising administering radiation.

20. The method of any one of embodiments 1-19, further comprising administering a second anticancer agent.

21. The method of embodiment 20, wherein the second anticancer agent is a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor.

EXAMPLES

The following examples are included for illustrative purposes only and are not intended to limit the scope of the invention.

Example 1: Colorectal Cancer Cell Survival Assay

Purpose: to assess the ability of different mitochondrial complex I inhibitors to inhibit colorectal cancer cell survival and to determine the half maximal inhibitory concentration ($IC_{50}$) for each compound.

Metformin is a mitochondrial complex I inhibitor that has been and is currently being tested assessed as a potential cancer treatment, although results using metformin have been mixed (Wang, et al, Drug Design, Development and Therapy, 2017, 11: 2421-2429). 5 m and AA6 are mitochondrial complex I inhibitors believed to bind to the quinone binding pocket of mitochondrial complex I (Ito, T. et al, Biochem. 2015, S4:3677-3686) and suppressor of site $I_Q$ electron leak (S1QEL) 1.1 is compound believed to bind site $I_Q$ in mitochondrial complex I (Brand et al. Cell Metabolism, 2016, 24: 582-592).

A. Methods

HTC116 cells were grown overnight at 37° C., 5% $CO_2$. Cells were then incubated for 72 hrs in humidified incubator at 37° C. and 5% $CO_2$ with 5 m, AA6, metformin, S1QEL 1.1, or cisplatin at concentrations ranging from 100 μM-50 nM. Each condition was done in triplicate, and the structures of the compounds were not known to the experimenters. After the incubation, cells were lysed with CellTiter-Glo® Luminescent Cell Viability Assay reagent (Promega) and luminescence was read using an Envision plate reader.

B. Results

Figure 1:
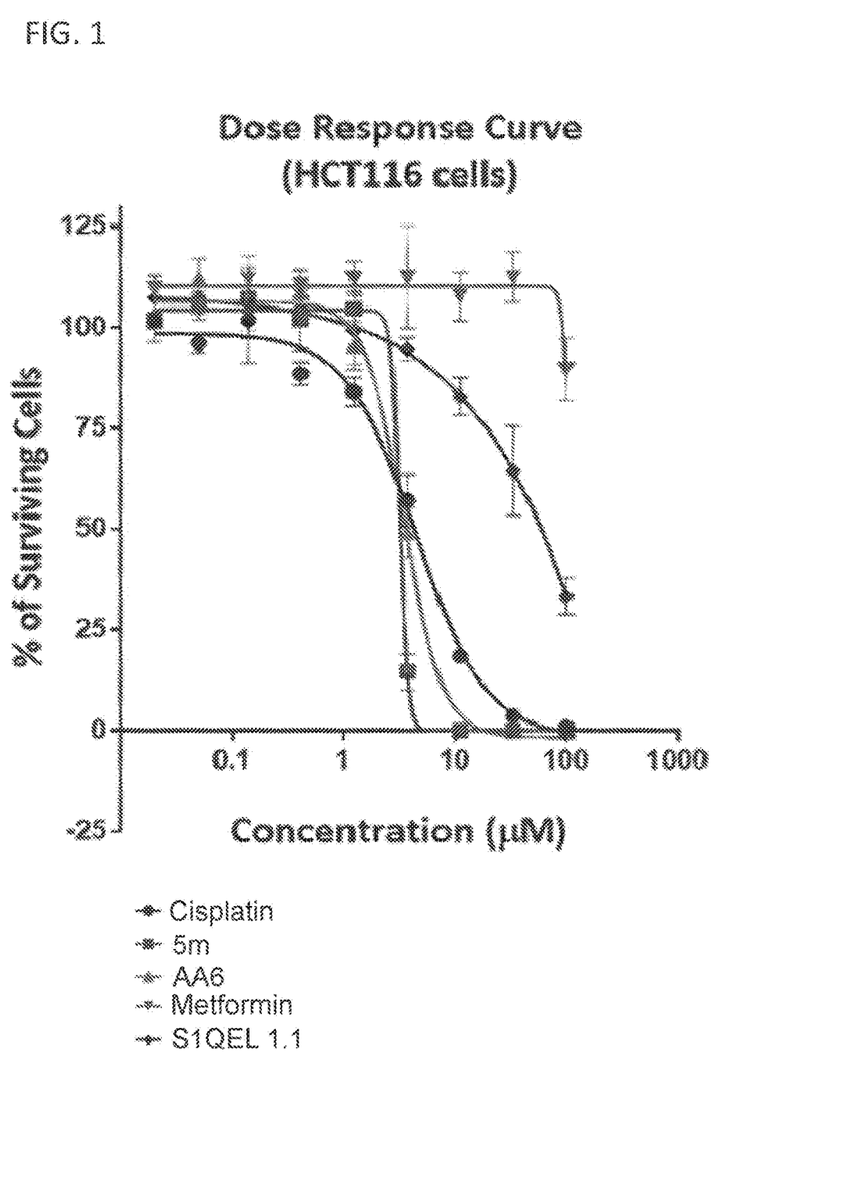
FIG. 1 shows dose response survival curves of HCT116 cells treated with cisplatin, 5 m, AA6, metformin, or S1QEL 1.1.

Cell viability plots for HTC116 are shown in FIG. 1 and calculated $IC_{50}$s for HTC116 are shown in Table 2. 5 m and AA6 demonstrated a similar ability to inhibit colorectal cancer cell survival as the cytotoxic drug cisplatin. The $IC_{50}$s of 5 m, AA6, and cisplatin were similar with 5 m and AA6 having slightly lower $IC_{50}$s. Metformin and S1Qel 1.1 had dramatically larger $IC_{50}$s than 5 m, AA6, or cisplatin. Cell viability was plotted with GraphPad Prism version 5 and the $IC_{50}$ was calculated for each compound. The graphical curves were fitted using a nonlinear regression model with a sigmoidal dose response.

TABLE 2

Absolute $IC_{50}$ for Cell Survival Assay using HTC116 Cell Line

| Compounds | $IC_{50}$ (μM) |
| --- | --- |
| Cisplatin | 4.3 |
| 5m | 3.2 |
| AA6 | 3.6 |
| Metformin | >100 |
| S1QEL 1.1 | 59.3 |

Example 2: Pancreatic Cancer Cell Survival Assay

Purpose: to assess the ability of mitochondrial complex I inhibitors 5 m, AA6, and metformin and the cytotoxic chemotherapy drug cisplatin to inhibit pancreatic cancer cell survival and to determine the half maximal inhibitory concentration ($IC_{50}$) for each compound. Pancreatic cancer is notoriously difficult to treat and can be resistant to cytotoxic chemotherapy drugs such as cisplatin.

A. Methods

PANC-1 and MiaPaCa-2 were grown overnight at 37° C., 5% $CO_2$ and 95% humidity. PANC-1 was grown in DMEM+ 10% FBS and MIA PaCa-2 was grown in DMEM+10%

FBS+2.5% H. Cells from each cell line were then incubated for 72 hrs in humidified incubator at 37° C. and 5% $CO_2$ with 5 m, AA6, metformin, or cisplatin at concentrations ranging from 100 µM-50 nM. Each condition was done in triplicate, and the structures of the compounds were not known to the experimenters. After the incubation, cells were lysed with CellTiter-Glo® Luminescent Cell Viability Assay reagent (Promega) and luminescence was read using an EnVision plate reader (PerkinElmer). Cell viability was plotted with GraphPad Prism version 5 and the $IC_{50}$ was calculated for each compound with each cell line. The graphical curves were fitted using a nonlinear regression model with a sigmoidal dose response.

B. Results

Figure 2A:
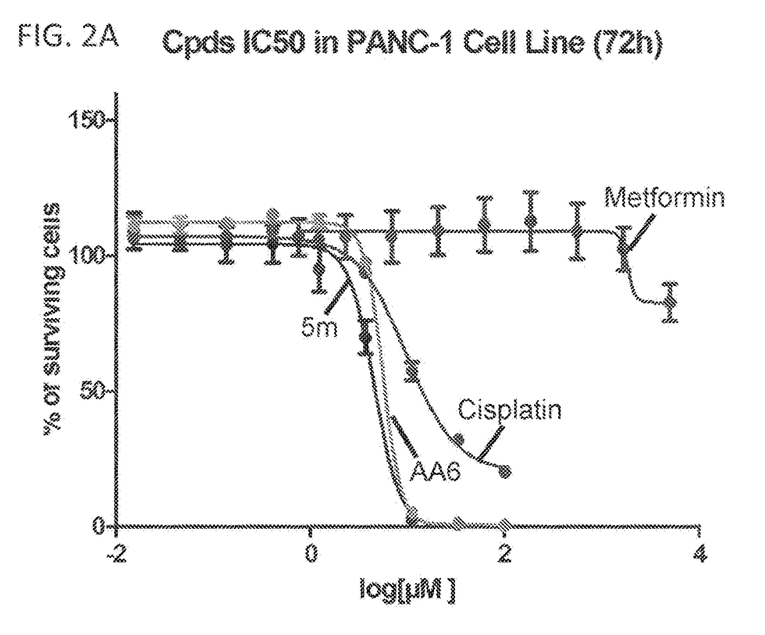
FIG. 2A-B show dose response survival curves of PANC-1 cells (FIG. 2A) or MiaPaCa-2 cells (FIG. 2B) treated with cisplatin, 5 m, AA6, or metformin.
Figure 2B:
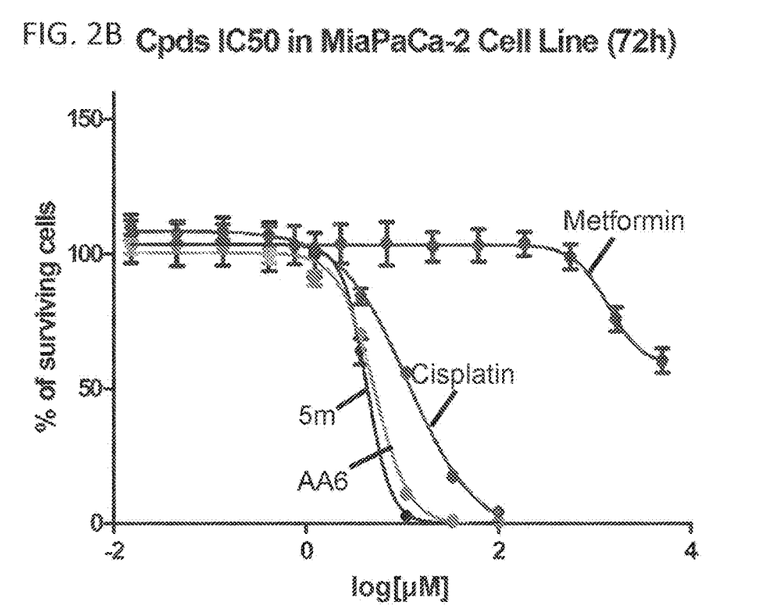

Cell viability plots for PANC-1 and MiaPaCa-2 are shown in FIGS. 2A-B and calculated $IC_{50}$s for PANC-1 are shown in Table 3 and for MiaPaCa-2 in Table 4. The $IC_{50}$ of cisplatin for PANC-1 was 12.2 µM and for MiaPaCa-2 was 14.2 µM. These results are consistent with the difficult to treat nature of pancreatic cancer, which is often resistant to treatment with cisplatin. Interestingly, the $IC_{50}$s for 5 m and AA6 remained below 6 µM, i.e. less than half the amount required for cisplatin.

TABLE 3

Absolute $IC_{50}$ for Cell Survival Assay using PANC-1 Cell Line

| Compound | Absolute $IC_{50}$ (µM) |
| --- | --- |
| 5m | 4.7 |
| AA6 | 5.9 |
| Metformin HCl | >5000 |
| Cisplatin | 14.2 |

TABLE 4

Absolute $IC_{50}$ for Cell Survival Assay using MiaPaCa-2 Cell Line

| Compound | Absolute $IC_{50}$ (µM) |
| --- | --- |
| 5m | 4.3 |
| AA6 | 5.1 |
| Metformin HCl | >5000 |
| Cisplatin | 12.2 |

Example 3: Hypoxic Cancer Cell Survival Assay

Purpose: determine the effect of hypoxic conditions on the ability of mitochondrial complex I inhibitors 5 m, AA6, and metformin to inhibit colorectal cancer cell survival and to determine the half maximal inhibitory concentration ($IC_{50}$) for each compound under hypoxic conditions.

One potential reason for the difficult to treat nature of pancreatic cancer is hypoxia. Pancreatic cancer has been shown to have a median tumor partial pressure of oxygen ($pO_2$) of 2.0-2.7 mmHg and a median % oxygen of 0.3-0.4%. Normal pancreatic tissue has been shown to have a $pO_2$ of 51.6 mmHg and a median % oxygen of 6.8%. These numbers translate into a 19.1-22.7 fold decrease in $pO_2$ between normal and cancerous pancreatic tissue (McKeown, Br J Radiol, 2014. 87:20130676). By contrast rectal carcinoma, a specific type of colorectal cancer, has been shown to have a median tumor $pO_2$ of 19.0-32.0 mmHg and a median % oxygen of 2.5-4.2. Normal rectal tissue has been shown to have a $pO_2$ of 52.0 and a median % oxygen of 6.8%. These numbers translate into only a 1.6-2.7 fold decrease in $pO_2$ between normal and cancerous rectal tissue (McKeown, Br J Radiol, 2014, 87:20130676).

A. Methods

HCT116 cells were cultured in an atmosphere of 37° C., 5% $CO_2$, 95% humidity, and with either 1% $O_2$ (hypoxic) or 20% $O_2$ (normoxic). No antibiotics were used in the cell culturing. HeLa cells were grown in parallel and samples were taken after 48 h and 72 h to confirm Hypoxia-inducible factor-1α (HIF-1α) expression by western blot.

HCT116 cells were then seeded on 6-well plates and incubated at 37° C., 5% $CO_2$, and 95% humidity overnight. Cells previously cultured under hypoxic conditions were again incubated with 1% $O_2$, and cells previously cultured under normoxic conditions were again incubated with 20% $O_2$.

Hypoxic and normoxic cells were then incubated for 72 hrs in humidified incubator at 37° C., 5% $CO_2$, 95% humidity, and either 1% $O_2$ (hypoxic) or 20% $O_2$ (normoxic) with 5 m, AA6, metformin, or cisplatin at concentrations ranging from 1 mM-50 nM. Each condition was done in triplicate, and the structures of the compounds were not known to the experimenters. After the incubation, cells were lysed with CellTiter-Glo® Luminescent Cell Viability Assay reagent (Promega) and luminescence was read using an EnVision plate reader (PerkinElmer). Cell viability was plotted with GraphPad Prism version 5 and the $IC_{50}$ was calculated for each compound with each cell line. The graphical curves were fitted using a nonlinear regression model with a sigmoidal dose response.

B. Results

Figure 3A:
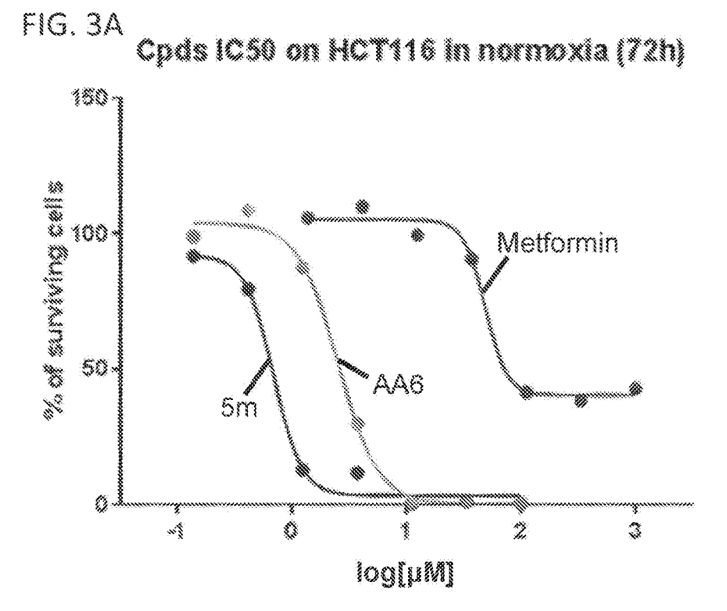
FIG. 3A-B show dose response survival curves of HCT116 cells treated with 5 m, AA6, or metformin under normoxic (FIG. 3A) or hypoxic (FIG. 3B) conditions.
Figure 3B:
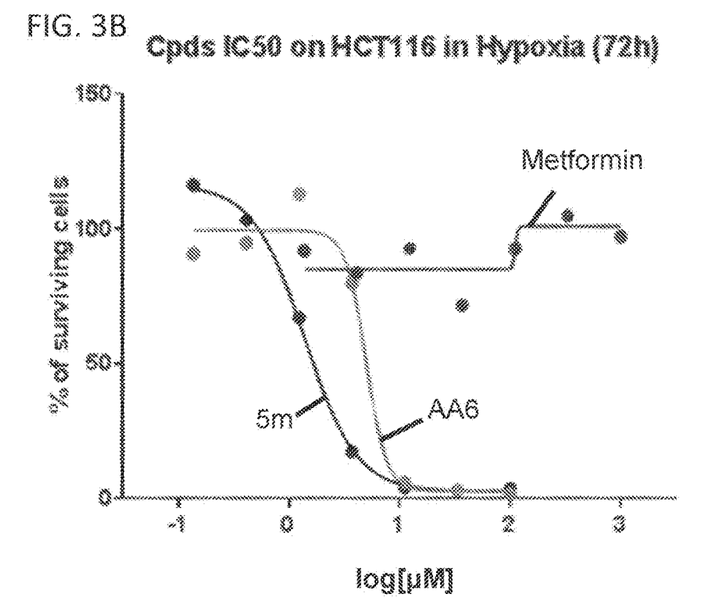

Cell viability plots for normoxic and hypoxic conditions are shown in FIGS. 3A-B and calculated $IC_{50}$s for normoxic conditions are shown in Table 5 and for hypoxic conditions in Table 6. As was seen for the pancreatic cell lines, the $IC_{50}$s for 5 m and AA6 remained below 6 µM. Interestingly, metformin treatment under normoxic conditions, although less effective than 5 m or AA6 treatment, resulted in a typical shaped dose response curve with an $IC_{50}$ of 71.8 µM, however, metformin treatment under hypoxic conditions failed to result in a recognizable dose response curve even with concentrations up to 1 mM.

TABLE 5

Absolute $IC_{50}$ for Cell Survival Assay using normoxic conditions

| Compound | Absolute $IC_{50}$ (µM) |
| --- | --- |
| 5m | 0.7 |
| AA6 | 2.6 |
| Metformin HCl | 71.8 |

TABLE 6

| Absolute IC₅₀ for Cell Survival Assay using hypoxic conditions | |
|---|---|
| Compound | Absolute IC$_{50}$ (μM) |
| 5m | 1.7 |
| AA6 | 5.0 |
| Metformin HCl | >1000 |

Example 4: Pharmacokinetic Parameters

Purpose: determine the pharmacokinetic (PK) parameters of 5 m in mice.

A. Method

Fed BALB/c mice were administered either 2 mg/kg of 5 m intravenously via the tail vein or 10 mg/kg of 5 m orally. For both conditions, 5 m was dissolved in 10% DMSO/50% PEG400/40% Water. Blood was sampled at various timepoints after the compound was administered and was analyzed using AB Sciex API 4000 LC/MS/MS in positive ion mode.

B. Results

Figure 4:
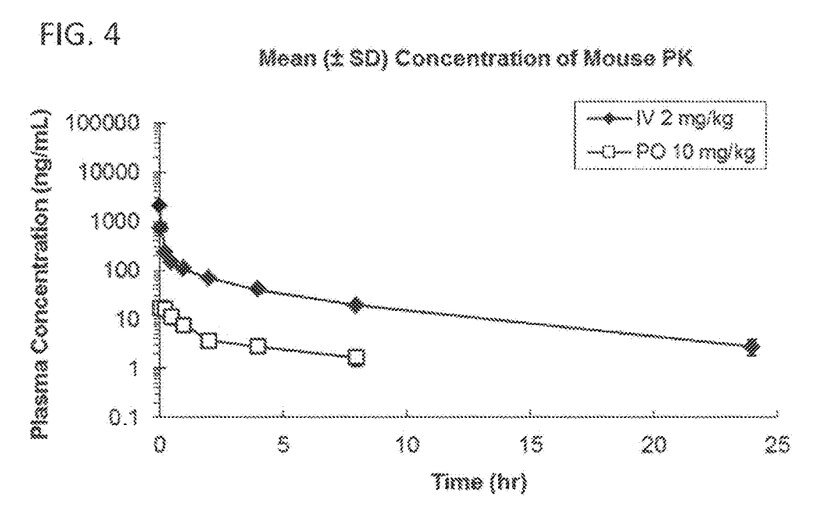
FIG. 4 shows the mean concentration of 5 m in plasma over time when administered intravenously or orally.

Administration of 5 m orally or intravenously at these concentrations did not result in any apparent abnormal symptoms or toxicity during the assay. Mean plasma concentrations over time are shown in FIG. 4, and calculated pk parameters are shown for IV administration in Table 7 and for oral administration in Table 8.

TABLE 7

| | | | | | PK Parameters for IV Administration | | | | |
|---|---|---|---|---|---|---|---|---|---|
| N = 3 | $t_{1/2}$ (hr) | $C_0$ (ng/mL) | AUC$_{last}$ (hr · ng/mL) | AUC$_{Inf}$ (hr · ng/mL) | AUC Extr (%) | $V_z$ (L/kg) | $V_{ss}$ (L/kg) | CL (mL/hr/kg) | MRT$_{Inf}$ (hr) |
| Mean | 5.30 | 3866 | 849 | 871 | 2.47 | 17.5 | 9.41 | 2302 | 4.10 |
| SD | 0.66 | 212 | 42 | 50 | 0.97 | 1.2 | 0.78 | 137 | 0.49 |
| CV % | 12.4 | 5.48 | 4.97 | 5.78 | 39.4 | 7.00 | 8.27 | 5.97 | 11.9 |

TABLE 8

| | | | | | PK Parameters for Oral Administration | | |
|---|---|---|---|---|---|---|---|
| N = 3 | $t_{1/2}$ (hr) | $C_{max}$ (ng/mL) | AUC$_{last}$ (hr · ng/mL) | AUC$_{Inf}$ (hr · ng/mL) | Vz/F (L/kg) | CL/F (mL/hr/kg) | F (%) |
| Mean | 3.62 | 18.3 | 32.8 | 41.5 | 1266 | 241750 | 0.773 |
| SD | 0.31 | 3.3 | 3.8 | 2.9 | 196 | 17130 | 0.089 |
| CV % | 8.45 | 18.0 | 11.5 | 6.98 | 15.4 | 7.09 | 11.5 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed is:

1. A method of treating cancer in a subject, comprising administering to the subject an effective amount of a compound of Formula (I):

or a tautomer thereof, or a salt of any of the foregoing, wherein:

X is halo;

Y is wherein:

* indicates the point of attachment to the carbonyl of the parent structure and ** indicates the point of attachment to (CH$_2$)$_{4-7}$—Z; and Z is C$_1$-C$_6$alkyl or phenyl, and wherein the cancer is associated with a hypoxic tumor.

2. The method of claim 1, wherein the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma.

3. The method of claim 1, wherein the cancer is pancreatic cancer or colorectal cancer.

4. The method of claim 1, wherein the hypoxic tumor is a solid tumor.

5. The method of claim 1, wherein a plurality of cells in the hypoxic tumor express one or more hypoxia-inducible factor (HIF) proteins; one or more messenger ribonucleic acids (mRNAs) encoding a HIF protein; or one or more hypoxia-inducible factor (HIF) proteins and one or more messenger ribonucleic acids (mRNAs) encoding a HIF protein.

6. The method of claim 5, wherein the one or more HIF proteins; the one or more mRNAs encoding a HIF protein; or the one or more HIF proteins and the one or more mRNAs encoding a HIF protein are expressed at a higher level than in a normal tissue.

7. The method of claim 1, wherein the hypoxic tumor has one or more of the following hypoxic conditions:
   (a) a median oxygen level below 2%;
   (b) a median partial pressure of oxygen ($pO_2$) of about or less than about 15 mmHg;
   (c) a median $pO_2$ that is less than 30% of the $pO_2$ of a normal tissue; and
   (d) a percentage of $pO_2$ measurements of the hypoxic tumor that equal less than 10 mm Hg ($HP_{10}$) is greater than 50%.

8. The method of claim 6, wherein the normal tissue is (a) non-cancerous muscle tissue; (b) derived from the same tissue or organ; or (c) healthy tissue located near the hypoxic tumor.

9. The method of claim 1, further comprising measuring the $pO_2$ or percent $O_2$ of the hypoxic tumor.

10. The method of claim 1, wherein the compound is or a tautomer thereof, or a salt of any of the foregoing.

11. The method of claim 1, wherein the compound is or a tautomer thereof, or a salt of any of the foregoing.

12. The method of claim 1, wherein the compound is administered orally or intravenously.

13. The method of claim 1, wherein the subject has had a prior treatment.

14. The method of claim 13, wherein the cancer is resistant or refractory to the prior treatment.

15. The method of claim 1, the cancer is resistant to treatment with gemcitabine, docetaxel, paclitaxel, paclitaxel protein-bound particles, cisplatin, or radiation.

16. The method of claim 1, further comprising administering radiation.

17. The method of claim 1, further comprising administering a second anticancer agent.

18. The method of claim 17, wherein the second anticancer agent is a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor.

19. A method of treating pancreatic or colorectal cancer in a subject, comprising administering to the subject an effective amount of a compound of Formula (I):

or a tautomer thereof, or a salt of any of the foregoing, wherein:
   X is halo;
   Y is wherein:
   * indicates the point of attachment to the carbonyl of the parent structure and ** indicates the point of attachment to $(CH_2)_{4-7}$—Z; and
   Z is $C_1$-$C_6$alkyl or phenyl.

20. The method of claim 19, wherein the cancer is pancreatic cancer.

21. The method of claim 19, wherein the cancer is colorectal cancer.

22. The method of claim 19, wherein the compound is or a tautomer thereof, or a salt of any of the foregoing.

23. The method of claim 19, wherein the compound is or a tautomer thereof, or a salt of any of the foregoing.

24. The method of claim 19, wherein the compound is administered orally or intravenously.

25. The method of claim 19, wherein the subject has had a prior treatment.

26. The method of claim 25, wherein the cancer is resistant or refractory to the prior treatment.

27. The method of claim 26, the cancer is resistant to treatment with gemcitabine, docetaxel, paclitaxel, paclitaxel protein-bound particles, cisplatin, or radiation.

28. The method of claim 19, further comprising administering to the subject radiation.

29. The method of claim 19, further comprising administering to the subject a second anticancer agent.

30. The method of claim 29, wherein the second anticancer agent is a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor.

* * * * *